United States Patent [19]

Fernandes et al.

[11] Patent Number: 4,623,717

[45] Date of Patent: * Nov. 18, 1986

[54] PASTEURIZED THERAPEUTICALLY ACTIVE PROTEIN COMPOSITIONS

[75] Inventors: Peter M. Fernandes, Lafayette; John L. Lundblad, El Cerrito, both of Calif.

[73] Assignee: Miles Laboratories, Inc., Elkhart, Ind.

[ * ] Notice: The portion of the term of this patent subsequent to Apr. 3, 2001 has been disclaimed.

[21] Appl. No.: 740,659

[22] Filed: Jun. 3, 1985

Related U.S. Application Data

[63] Continuation-in-part of Ser. No. 202,508, Oct. 31, 1980, which is a continuation-in-part of Ser. No. 127,351, Mar. 5, 1980, abandoned.

[51] Int. Cl.$^4$ ............ A61K 35/16; A61K 37/02; A61K 37/06; C07K 3/28
[52] U.S. Cl. .................... 530/380; 424/101; 424/85; 514/8; 514/21; 530/381; 530/382; 530/383; 530/386; 530/393; 530/830; 435/188
[58] Field of Search ............... 260/112 R, 112 B, 121; 424/85, 101; 435/188; 530/383, 393, 382, 381, 380, 386; 514/8, 21

[56] References Cited

U.S. PATENT DOCUMENTS

| | | | |
|---|---|---|---|
| 4,061,735 | 12/1977 | Funakoshi et al. | 424/101 X |
| 4,137,307 | 1/1979 | Funakoshi et al. | 260/112 B X |
| 4,279,344 | 10/1981 | Schwinn | 260/112 B |
| 4,440,679 | 4/1984 | Fernandes et al. | 260/112 R X |

*Primary Examiner*—Howard E. Schain
*Attorney, Agent, or Firm*—James A. Giblin

[57] ABSTRACT

Compositions containing thermally sensitive, therapeutically active proteins are pasteurized without substantial loss of therapeutic activity by mixing the protein composition with a pasteurization-stabilizing amount of a sugar or reduced sugar and of an amino acid prior to pasteurization. Pasteurized compositions containing therapeutically active proteins, which have heretofore been unattainable, can be prepared by the method of the invention.

19 Claims, No Drawings

PASTEURIZED THERAPEUTICALLY ACTIVE PROTEIN COMPOSITIONS

CROSS-REFERENCES TO RELATED APPLICATIONS

This is a continuation-in-part of U.S. patent application Ser. No. 202,508, filed Oct. 31, 1980, which is a continuation-in-part of U.S. patent application Ser. No. 127,351, filed Mar. 5, 1980, now abandoned.

BACKGROUND OF THE INVENTION

1. Field of the Invention

This invention relates to and has among its objects novel compositions for therapeutic use and methods of making them. It is a particular object of this invention to provide pasteurized compositions containing therapeutically active proteins. Further objects of the invention will be evident from the following description wherein parts and percentages are by weight unless otherwise specified.

2. Description of the Prior Art

Many useful blood fractions and blood proteins are obtained from human blood plasma by fractionation according to known techniques such as, for example, the alcohol fractionation method of Cohn described in U.S. Pat. No. 2,390,074 (1945) and the *Journal of the American Chemical Society*, Vol. 68, page 459 (1946) and the Rivanol ® ammonium sulfate method. The aforementioned methods as well as other variations and techniques are summarized in "The Plasma Proteins", second edition, Volume III, pages 548-550, Academic Press, New York, N.Y. (1977). These blood fractions contain biologically active proteins that possess certain therapeutic qualities. For instance, Factor VIII or antihemophilic factor is useful against hemophilia; plasminogen is a precursor of plasmin for treatment of acute thromboembolic disorders; immune serum globulin (IgG) is employed in the treatment of congenital gamma globulin deficiency, measles, poliomyelitis and hepatitis A and B; fibronectin has been identified as active in treatment of burns, shock, cancer, etc.; antithrombin III is a coagulation inhibitor, cryoprecipitate itself may be used directly for classic hemophilia; Plasma Protein Fraction (human) and albumin are useful in treatment of shock due to burns, crushing injuries, abdominal emergencies, and any other cause producing a predominant loss of plasma fluids and not red cells; immune globulin, intravenous (modified immune serum globulin) is a substitute for immune serum globulin administerable in larger quantities; Factor VIII inhibitor bypassing active (FEIBA) substance described in U.S. Pat. No. 4,160,025 as a blood-coagulation-promoting preparation for Factor VIII inhibitor patients; alpha-1-antitrypsin can be employed in the treatment of emphysema; plasma growth hormone corrects pituitary growth deficiency, somatomedin is useful in correcting growth deficiencies, other immune serum globulins, e.g., IgA, IgD, IgE, and IgM, may be employed to treat various immune protein deficiencies; prealbumin (U.S. Pat. No. 4,046,877) is employed to increase immunologic competence; plasminogen-streptokinase complex (U.S. Pat. No. 4,178,368) can be administered to patients for treatment of thromboembolisms; ceruloplasmin, transferrin, haptoglobin, and prekallikrein have reagent and other uses.

One problem confronting users of plasma, plasma fractions, and compositions containing individual blood proteins is the thermal instability of the therapeutically active proteins contained therein. In many cases, substantial, and sometimes complete, losses of activity are observed if these proteins are heated above physiological temperatures, i.e., above about 40°-45° C. Consequently, these items require special care during preparation and storage to minimize such deactivation.

The thermal instability of the aforementioned proteins renders them unpasteurizable. Therapeutically active proteins isolated from plasma may contain viruses, e.g., hepatitis virus, present in the source material for the protein fraction, namely, blood from a donor. A risk of contracting hepatitis exists, therefore, for those receiving unpasteurized fractions from blood plasma fractionation because the presence of the virus cannot be detected with certainty by any known procedure. In a large number of situations, this risk is outweighed by the detriment to a patient in not receiving the therapeutic plasma fraction as determined by the physician.

Some therapeutically active proteins derived from plasma have been pasteurized successfully. For example, it is well known that albumin can be pasteurized by heating at 60° C. or 64° C. for 10 hours (Gellis et al, *J. Clin. Invest.*, Vol. 27, pages 239-244 [1948]) in the presence of certain stabilizers such as acetyl-tryptophan and sodium caprylate. Individuals receiving this pasteurized material did not contract hepatitis, thus indicating the inactivation of hepatitis virus while retaining the activity of albumin under the afore-described heating conditions. Plasma Protein Fraction (human) is also stabilized during pasteurization by the above method.

A process for pasteurizing plasminogen is disclosed by Baumgarten et al in U.S. Pat. No. 3,227,626. An aqueous preparation containing 0.25-20 milligrams per milliliter (mg/ml) of plasminogen and further containing 0.1-0.5 molar lysine with a pH of 5.3-7.5 was heated at 60° C. for 10 hours. As the patentee states, hepatitis virus was destroyed and the danger of transmitting hepatitis was removed with retention of plasminogen activity. Attempts to pasteurize plasminogen under the above conditions in the absence of lysine resulted in complete destruction of plasminogen cannot be stabilized with N-acetyl-tryptophan and sodium caprylate during pasteurization, nor can albumin and Plasma Protein Fraction (human) be pasteurized in the presence of lysine.

Singher has described a process for treating plasminogen to produce a material that is not contaminated with hepatitis virus (U.S. Pat. No. 2,897,123). In the patented pasteurization technique aqueous solutions of plasminogen are heated at about 60° C. for about 10 hours. The activity of plasminogen is retained if the solutions have a pH in the range not less than 3 nor greater than 6.5 and an ionic strength not greater than 0.3.

Another method for removing hepatitis virus from a biological material is described in U.S. Pat. No. 4,168,300. The material to be treated is contacted with a preparation, which may be agarose gel or beaded polyacrylamide plastic coupled with a variety of hydrophobic ligands. Plasma and albumin were subjected to the above purification technique to remove hepatitis virus.

Aqueous solutions of the enzyme thrombin have been stabilized (Seegers, *Arch. Biochem.*, 1944, Vol. 3, pages 363-367) during heating. at 50° C. in the presence of saturation amounts of certain glycosides. The stabilized solutions were heated at the above temperature for a period of 48 hours or more with minimal loss of activity. On the other hand, Seegers also discloses that glycosides and polyols have only minimal effectiveness in stabilizing the enzyme prothrombin. The reversible denaturation of lysozyme and ribonuclease was studies by Gerlsma et al, *Int. J. Peptide Protein Res.*, Vol. 4, pages 377-383 (1972). The authors found that certain polyhydric alcohols increased somewhat the temperatures at which these enzymes were denatured. Finally, Simpson et al, in *J. Am. Chem. Soc.*, Vol. 75, No. 21, pages 5139-5152 (1953) and Donovan in *J. Sci. Fd. Agric.*, Vol. 28, pages 571-578 (1977) noted that the denaturation temperature of ovalbumin (an egg white protein) was raised slightly in the presence of sucrose in aqueous solutions of the protein. However, Donovan points out that the temperatures of denaturation of ovalbumin and S-ovalbumin are 84.5° C. and 92.5° C., respectively. Furthermore, ovalbumin and S-ovalbumin, as well as the aforementioned enzymes, have no therapeutic activity in treating disorders in humans, whereas blood plasma proteins are therapeutically active. In fact, as mentioned below, proteolytic enzymes deactivate blood plasma proteins.

Singher, in the aforementioned U.S. Patent, lists some methods of destroying hepatitis virus. The least effective of these methods involves the use of either nitrogen mustard or beta-propiolactone. High energy irradiation in appropriate dosage is effective but destroys biological activity when applied to human blood products. Heat is recognized also as effective against hepatitis virus, the preferred treatment being heating the material at 60° C. for 10 hours. Higher temperatures above 70° C. for shorter intervals or lower temperatures for longer intervals have also been tried with successful results. However, it is important to note that higher temperatures are undesirable because of the potential for denaturation of the proteins. Furthermore, lower temperatures for long intervals are to be avoided because various proteolytic enzymes are activated under these conditions, and these activated enzymes cause protein degradation. Also, the use of temperatures lower than 60° C. for pasteurization has not been shown to consistently yield a material that does not contain the infective virus.

As mentioned above, the recognition that heating at 60° C. and 64° C. for 10 hours successfully destroys the hepatitis virus in albumin was made by Gellis et al, supra. Gellis et al proved experimentally that albumin heated under the above conditions did not transmit hepatitis even if hepatitis virus was present prior to pasteurization. However, the author noted that hepatitis virus survived heating at 56° C. for one hour, a temperature usually employed for the inactivation of viruses. Thus, although heating at temperatures of about 56° C. for one hour will deactivate most viruses, hepatitis virus is not inactivated; and materials containing hepatitis virus, which are heated at 56° C. for one hour, cause infection of hepatitis in individuals receiving such materials.

SUMMARY OF THE INVENTION

The invention described herein provides means for obviating the above-outlined problems. In the method of the invention certain compositions containing thermally sensitive, therapeutically active proteins are rendered heat stable during pasteurization or heating at a temperature of about 60°-75° C. by mixing with heat-stabilizing, or pasteurization-stabilizing, amounts of a sugar or reduced sugar and an amino acid. Pasteurized compositions containing therapeutically active proteins heretofore unobtainable are available as a result of the process of our invention by heating a mixture of unpasteurized protein composition, a sugar or reduced sugar and an amino acid suspended or solubilized usually in an aqueous medium at a temperature and for a time sufficient to pasteurize the protein composition. Following pasteurization or heat treatment, the sugar or reduced sugar and amino acid are removed totally or in part, as desired, from the protein composition by conventional techniques, and the pasteurized protein composition is processed according to conventional procedures for its ultimate therapeutic use.

The primary advantage of the invention is the availability of thermally stable and pasteurized therapeutically active protein compositions, which heretofore have been unknown and unattainable. Since the therapeutically active protein compositions of the invention can be heated with minimal loss of activity under conditions known to inactivate hepatitis virus, these valuable materials can be administered to patients, who can obtain the full therapeutic benefits thereof with a substantially reduced risk of being infected by the hepatitis virus.

Another advantage of the invention is that it may be applied to blood plasma prior to fractionation, to partially fractionated blood plasma, and to individual blood plasma fractions, as well as to individual blood plasma proteins themselves. Thus, the versatility of the present process can be seen. Pasteurization of blood plasma prior to fractionation allows fractionation techniques other than the Cohn process to be applied to whole plasma.

DESCRIPTION OF THE PREFERRED EMBODIMENTS

As mentioned above, the products of the invention include pasteurized or heat-treated compositions comprising a thermally sensitive, therapeutically active protein capable of being stabilized during pasteurization or heating at temperatures of about 60°-75° C., preferably about 60°-70° C. when mixed with thermal-stabilizing, or pasteurization-stabilizing, amounts of a sugar or reduced sugar and of an amino acid, the pasteurized compositions containing or being free of sugar or reduced sugar and amino acid.

In the method of the invention, the protein composition to be pasteurized is suspended or dissolved in an aqueous medium with an amount of sugar or reduced sugar and of amino acid sufficient to stabilize the protein composition during subsequent pasteurization. The concentration of sugar or reduced sugar and of amino acid necessary to stabilize a protein composition in accordance with this invention depends on the type and concentration of therapeutically active protein in the protein composition, on the type of sugar or reduced sugar used, and on the amino acid used. The therapeutically active protein is considered to be stabilized if it retains a substantial portion, i.e., at least 40%, of its therapeutic activity during pasteurization. It is preferred that 70% or more of the therapeutic activity of the protein composition be retained during pasteurization. Consequently, the amount of sugar or reduced sugar and of amino acid to be added should be such as to retain the above-recited amount of therapeutic activity.

Typical examples of sugars that may be employed in our method are mono-, di-, and trisaccharides such as arabinose, glucose, galactose, fructose, ribose, mannose, rhamnose, sucrose, maltose, raffinose, melezitose, and so forth. Exemplary of reduced sugars included within the purview of the invention are erythritol, ribitol, sylitol, sorbitol, mannitol, etc. Preferably, the sugar or reduced sugar should be water miscible and physiologically compatible with the protein and have a low molecular weight, i.e. a molecular weight less than about 5000. Generally, the amount of sugar or reduced sugar used in combination with amino acid to stabilize the protein composition during subsequent pasteurization should be at least about 0.8 g/ml (54% w/v, 45% w/w) based on total aqueous solution or suspension of the protein composition, sugar or reduced sugar and amino acid. A useful range of amounts of sugar or reduced sugar in the method of the invention is about 0.8 g/ml to about 1.5 g/ml. Although the mentioned useful range is preferred, still greater amounts of sugar or reduced sugar may be used to achieve the advantages of the method of the invention. Sucrose is preferred as the sugar or reduced sugar compound.

As the amino acid one may employ lysine, arginine, leucine, isoleucine, methionine, phenylalanine, threonine, tryptophan, valine, alanine, aspartic acid, cysteine, glutamic acid, glycine, histidine, proline, serine, tyrosine, and the like and mixtures thereof. Substances producing the aforesaid amino acids such as an amino acid salt and the like also may be used. It should be understood that amino acids in the absence of a sugar or reduced sugar are not effective pasteurization-stabilizing agents for those protein compositions that have been unpasteurizable prior to this invention. Generally, the amount of amino acid used in combination with sugar or reduced sugar during subsequent pasteurization may be in the range of about 0.05 M to about 0.8 M, preferably about 0.1 M to about 0.65 M, based on aqueous solution of protein composition, sugar or reduced sugar and amino acid, of at least one amino acid. At least one of arginine, lysine and glycine is preferred as the amino acid.

Generally, the amount of protein composition in the aqueous mixture of protein composition with sugar or reduced sugar and amino acid will be in the range of about 1 mg/ml to about 15 mg/ml. However, the amount of protein composition is not believed to be critical.

After the protein composition has been mixed with the sugar or reduced sugar and amino acid, the mixture is heated at a temperature and for a time sufficient to pasteurize it. Thus, the mixture is pasteurized upon heating it under conditions known to inactivate hepatitis virus. Effective pasteurization to inactivate hepatitis virus and to substantially reduce the risk of hepatitis infection is obtained by heating an unpasteurized protein composition at a temperature of about 60°–75° C., preferably about 60°–70° C. for a period of about 10 hours, usually about 62°–65° C. for about 10 hours.

The pasteurization is carried out under pH conditions which approximate physiological conditions. Thus, the pH of the mixture usually should be within the range of about 5.5–8.0, preferably about 6.0–7.5. The general, physiological conditions are desirable, where possible, during pasteurization to insure the least disturbance to the therapeutically active protein composition.

The amounts of a particular sugar or reduced sugar and amino required to stabilize a specific protein composition during pasteurization and the conditions necessary to pasteurize the composition can be determined readily by one skilled in the art using pilot trials in accordance with the teaching contained herein.

Following pasteurization the mixture of sugar or reduced sugar, amino acid and protein composition may be treated to remove all or part of the sugar or reduced sugar and amino acid. Conventional techniques can be employed to achieve this end. For example, the mixture can be dialyzed or diafiltered using an appropriate semipermeable membrane. Other means of removing the sugar or reduced sugar and amino acid will be suggested to those skilled in the art.

The pasteurized mixture may be treated to remove water therefrom by procedures well known in the art. For instance, the mixture can be freeze-dried or ultrafiltered and then freeze-dried. Furthermore, the mixture can be sterile-filtered by conventional methods prior to water removal.

The pasteurized protein compositions of the invention can be formulated into pharmaceutical preparations for therapeutic use. To prepare it for intravenous administration the protein composition is dissolved usually in water containing physiological substances such as sodium chloride, glycine, and the like and having a buffered pH compatible with physiological conditions. Generally, guidelines for intravenously administered protein compositions are established by governmental regulation.

Thermally sensitive, therapeutically active proteins included within the scope of the invention are those proteins generally administered to patients for preventative and/or curative purposes, which lose some therapeutic activity when heated above about 40°–45° C. and which are capable of being stabilized during pasteurization or heating at a temperature of about 60°–75° C. in the presence of a polyol (i.e. a polyhydroxyl compound, for example, polyhydric alcohols and carbohydrates such as sugars). Examples of therapeutically active proteins that may be pasteurized in accordance with the present invention, by way of illustration and not limitation, are those proteins derived from venous blood plasma or placental plasma and include blood plasma, partially fractionated blood plasma proteins. Thus, for example, protein compositions pasteurizable by the method of the invention may include as the therapeutically active protein plasminogen, albumin, antihemophilic factor (Factor VIII), Plasma Protein Fraction (human), fibronectin (cold insoluble globulins), an immune serum globulin such as IgG, IgA, IgD, IgE, and IgM, high molecular weight kininogen (90,000–106,000), an immune globulin, intravenous (modified, either chemically or enzymatically or by fractional separation, immune serum globulin), FEIBA, antithrombin III, alpha-1-antitrypsin, plasma proteins (molecular weight 1000–30,000) having growth activity such as plasma growth hormone, somatomedin, prealbumin, plasminogen-streptokinase complex, ceruloplasmin, transferrin, haptoglobin, and prekallikrein, etc., and mixtures thereof. In addition, pasteurized compositions containing "defatted" albumin and "defatted" Plasma Protein Fraction (human), i.e., PPF (human), are available through the invention. The term "defatted" means that the albumin and PPF (human) contain no more fatty acid material than that present in the native state prior to pasteurization. The pasteurized defatted compositions can be administered to patients who cannot tolerate infusion of high fatty acid material such as that obtained using standard pasteurization stabilizing agents, namely, sodium caprylate and sodium acetyl-tryptophanate.

It is noteworthy that antihemophilic factor B (Factor IX) and prekallikrein activator cannot be pasteurized in the presence of a polyol in accordance with the above method. Indeed, these proteins lose substantially all their therapeutic activity under conditions under which the aforementioned protein compositions retain a substantial portion of their activity.

In particular, the method of this invention is directed to pasteurizing a composition comprising a thermally sensitive, therapeutically active protein selected from the group consisting of antihemophilic factor (Factor VIII, fibronectin, antithrombin III, alpha-1-antitrypsin, and prekallikrein. The antihemophilic factor protein which may be treated according to the method of this invention can be prepared according to any of the well-known, conventional techniques such as, for example, the technique disclosed in any of the following: Hershgold et al, *J. Lab. and Clin. Med.*, 67, 23–32 (1966); and Mozen, *Rev. Hematol.*, 1, 135–160 (1980). Fibronectin can be prepared by the method described by Engvall et al, *Int. J. Cancer*, 20, 2 (1977). Cohn Effluent II+III, which contains as major protein components antithrombin-III and alpha-1-antitrypsin, can be prepared by the alcohol fractionation method described in Cohn, U.S. Pat. No. 2,390,074 and *J. Amer. Chem. Soc.*, 68, 459 (1946). Prekallikrein can-be prepared from plasma by, for example, first treating the starting plasma to lower the ionic strength, applying the plasma to a DEAE Sephadex® A-50 column, collecting and pooling the eluate containing prekallikrein peaks, contacting the prekallikrein pool with conconavalin A-Sepharose, and eluting purified prekallikrein from the conconavalin A-Sepharose.

It has been found that the fibrinogen (Factor I) content of the protein composition to be pasteurized is an important factor, the higher the fibrinogen content, the greater the amount of sugar or reduced sugar needed. The fibrinogen content of the protein composition should be no greater than about 60%, based on the weight of total protein, or no greater than 0.6% based on the weight of solution at, for example, 54% sucrose (weight to volume). In a preferred embodiment the protein composition should contain no greater than 40% fibrinogen, based on the weight of solution. If the amount of fibrinogen in the composition to be pasteurized exceeds the above limits and the amount of sugar or reduced is not increased, the thermal stability imparted to the therapeutically active proteins by the sugar or reduced sugar is substantially reduced or lost completely.

A protein composition having a fibrinogen content greater than 60% can be pasteurized in accordance with our method (1) if the concentration of fibrinogen in the solution is below 0.6%, preferably below 0.4%, or (2) if a protein capable of being stabilized during pasteurization such as albumin and the like is first added to the protein composition to lower its fibrinogen content to less than 60% (the added protein generally should have the characteristic of being easily separable from the initial protein composition if necessary; it may be also that the added protein is compatible with the intended therapeutic use of the initial protein composition and, thus, need not be removed therefrom), or (3) if at least about 5 parts of sugar or reduced sugar are used per part of fibrinogen.

Important products of this invention include pasteurized aqueous mixtures of therapeutically active protein compositions which may contain or be free of sugar or reduced sugar and amino acid and those pasteurized protein compositions being free of sugar or reduced sugars and amino acid and water. Pharmaceutical preparations containing therapeutic amounts of a protein composition pasteurized in accordance with the present invention are also contemplated. Particular products of the invention include pasteurized compositions containing antihemophilic factor (Factor VIII), fibronectin, alpha-1-antitrypsin, antithrombin III and prekallikrein.

As mentioned above the pasteurized products of the invention may be incorporated into pharmaceutical preparations, which may be used for therapeutic purposes. However, the term "pharmaceutical preparation" is intended in a broader sense herein to include preparations containing a protein composition pasteurized in accordance with this invention used not only for therapeutic purposes, but also for reagent purposes as known in the art; for tissue culture wherein organisms such as viruses for the production of vaccines, interferon, and the like, are grown on plasma or on plasma fractions, e.g., Cohn Effluent II+III, Cohn Fraction IV, Cohn Fraction V, and so further; etc.

For any of the above uses it is advantageous that the protein composition be free of infective hepatitis as provided in the instant invention. The pharmaceutical preparation intended for therapeutic use should contain a therapeutic amount of a pasteurized protein composition, i.e., that amount necessary for preventative or curative health measures. If the pharmaceutical preparation is to be employed as a reagent, then it should contain reagent amounts of pasteurized protein composition. Similarly, when used in tissue culture or a culture medium the pasteurized protein composition should contain an amount of protein composition sufficient to obtain the desired growth. It should be obvious that protein compositions pasteurized in accordance with this invention will not contain infective amounts of viruses and other organisms which are inactivated under the pasteurization conditions.

The invention described above is demonstrated further by the following illustrative examples.

EXAMPLE 1

Effect of Sugar Concentration on Stability of Antihemophilic Factor

This experiment was carried out to determine the effect of increasing concentrations of sugar on the stability of antihemophilic factor (also referred to as AHF or Factor VIII) upon heating at pasteurization conditions. An antihemophilic factor concentrate (commercially available from Cutter Laboratories, Berkeley, CA as KOATE® brand of antihemophilic factor) was reconstituted in sterile water for injection ("WFI") to give samples having an $A_{280}$ of 14.8, 7.05, 3.4, 1.8, and 0.98. To aliquots of each of the samples having the given protein concentration ($A_{280}$) was added 0.8 (54% w/v, 45% w/w), 1.0 (62% w/v, 50% w/w), 1.2 (70% w/v, 55.6% w/w), and 1.5 (77% w/v, 59.9% w/w) g/ml of sucrose. Each of the samples was heated at pasteurization conditions of 10 hours at 60° C. It was observed that only samples containing 54% added sucrose and having an $A_{280}$ of 14.8, 7.05, 3.4 and 1.8 became hazy. These data indicate that a sucrose concentration, representative of concentration of sugars and reduced sugars, of 54% (w/v) is the minimum concentration of sugar required to provide advantageous stability to heat of the thermally sensitive, therapeutically active proteins selected from AHF, fibronectin, antithrombin-III, alpha-1 antitrypsin and prekallikrein.

EXAMPLE 2

Effect of High Sugar Concentration and Amino Acid on Stability of Antihemophilic Factor This experiment was carried out to further demonstrate the importance of increased sugar or reduced sugar concentrations combined with amino acid on the stability of AHF upon heating at pasteurization conditions. Test samples of the AHF concentrate described in experiment 1 above were reconstituted in sterile WFI. To each sample was added sodium citrate (0.1 M), glycine (0.3 M) and sodium chloride (0.15 M). Sucrose was added to the samples at a concentration of 1.2 g/ml (70% w/v, 55.6% w/w) and 0.8 g/ml (54% w/v, 45% w/w). The $T_{580}$ (transmittance) of the samples was measured and used as the basis for determining the degree of protein (AHF) denaturation upon pasteurization, water reference $T_{580}$ being 100%. Each of the samples was heated at pasteurization conditions for 10 hours at 60° C. The results are given below.

| Sample | Sucrose Concentration | $T_{580}$ | % AHF Recovery* |
|---|---|---|---|
| Test #1 | 1.2 g/ml | 94% | 66.0% |
|  | 0.8 | 68% | 23.8% |
| Test #2 | 1.2 | 96% | 69.4% |
|  | 0.8 | 86% | 38.5% |
| Test #3 | 1.2 | 95% | 61.7% |
|  | 0.8 | 79% | 51.4% |

*Recovery determined by analysis for procoagulant activity by the methods of Langdell et al, J. Lab. Clin. Med., 41, 637 (1953) and Proctor et al, Am. J. Clin. Path., 36, 212 (1961).

It was observed that in each of the tests, #1–3, recovery of AHF was greater with the higher concentration of sucrose, the average recovery of AHF being 65.7% with 1.2 g/ml of sucrose and 37.9% with 0.8 g/ml of sucrose. The average $T_{580}$ of 95% with the use of 1.2 g/ml of sucrose compared with the average $T_{580}$ of about 78% with the use of 0.8 g/ml of sucrose gave evidence that a marked decrease in denaturation of AHF under the pasteurization conditions occurred with the use of the higher than with the lower sucrose concentration, each in combination with the glycine concentration of 0.3 M. These data indicate that the use of higher concentrations of sucrose, representative of concentration of sugars and reduced sugars, in combination with a lower concentration of glycine as the amino acid stabilizer against heat than was heretofore known, provides for advantageous recovery of AHF upon heating at pasteurization conditions for 10 hours at 60° C.

EXAMPLE 3

Effect of 77% (w/v) Sugar Concentration and Amino Acid on Stability of Antihemophilic Factor The experiment described in Example 2 above was repeated except that sucrose was added at a concentration of 1.5 g/ml (77% w/v, 59.9% w/w) in place of the concentration of 1.2 g/ml described in Example 2 to determine whether further improvement in AHF recovery could be achieved using sucrose concentrations greater than 1.2 g/ml. In several attempts, VIII:C analysis was made difficult by the crystallization of sucrose during freezing and thawing. In another experiment as described in Example 2 except that an AHF preparation containing 1.5 g/ml of sucrose, 0.01 M sodium citrate and 0.3 M glycine and having an $A_{280}$ of 10 which was prepared as described by Mozen, Rev. Haematol., 1, 135 (1980) at pages 144–145 wherein the "supernatant", also known as the acid-chill effluent, was adjusted to an acid pH value, the % AHF recovery was 80%.

EXAMPLE 4

Effect of pH, High Sugar Concentration and Amino Acid on Recovery of Antihemophilic Factor This experiment was carried out to determine the effect of pH on the recovery of AHF upon pasteurization and to illustrate the effect of the combination of higher sugar concentration and lower glycine concentration than was heretofore known. An antihemophilic factor (AHF, or Factor VIII) solution was prepared by the method of Mozen, Rev. Hematol., 1, 135–160 (1980). To the solution so prepared was added 0.01 M sodium citrate and 0.3 M glycine and then the solution was diluted with WFI to an $A_{280}$ of 25. Aliquots of this solution were taken and the pH of the aliquots was adjusted with sodium hydroxide or hydrochloric acid to the values shown in the table below. Aliquots with lysine added to give a solution 0.32 M in lysine and without lysine were treated with 1.2 g/ml of sucrose to provide test samples having a sucrose concentration of 70% w/v (55.6% w/w) based on starting solution. All aliquots were heated at pasteurization conditions for 10 hours at 60° C. Control aliquots were prepared as above but were held at 5° C. during this time. Control and pasteurized samples were analyzed for recovery of procoagulant activity by the methods of Langdell et al, J. Lab. Clin. Med., 41, 637 (1953) and Proctor et al, Am. J. Clin. Path., 36, 212 (1961). The results are given below:

|  | % Recovery of AHF | |
|---|---|---|
| pH | 0.32 M lysine | No lysine |
| 6.55 | 100% | 85% |
| 6.9 | 93% | 66% |
| 7.2 | 86% | 48% |
| 7.6 | 62% | 68% |

These data indicate that carrying out the pasteurization at a pH in the range of 6.0–7.5, preferably 6.55, using as the heat stabilizer a combination of 0.3 M glycine and 0.32 M lysine with a sucrose concentration of 70% w/v (55.6%, w/w), affords advantageous stability to heat of AHF that was heretofore not known. Although the mechanism by which this improvement is achieved is not fully understood, the data suggests that pasteurization conditions at a pH that is compatible with AHF and also that is remote from the optional pH at which proteolytic enzymes may operate to diminish AHF procoagulant activity may afford higher recovery of AHF.

EXAMPLE 5

Effect of Varying Amino Acid Concentration with High Sugar Concentration on Recovery of Antihemophilic Factor This experiment was performed to further determine and characterize the effect of the combination of lower concentrations of amino acid, particularly the mixture of lysine and glycine, with higher sucrose concentrations than was known heretofore. An AHF solution was prepared by the method of Mozen, *Rev. Hematol.*, 1, 135-160 (1980). To the solution so prepared there was added 0.005 M sodium citrate and 0.16 M glycine. Then, the solution was adjusted to pH 6.9 and diluted with WFI to an $A_{280}$ of 21. Aliquots of this solution were taken and lysine concentration in the aliquots was varied. To the aliquots was added 1.2 g/ml of sucrose and the resulting solutions were heated at pasteurization conditions for 10 hours at 60° C. The results are given below:

| Lysine | % AHF recovery |
|---|---|
| 0 | 76.5% |
| 0.04 M | 76.5% |
| 0.08 M | 68.2% |
| 0.16 M | 80.6% |
| 0.32 M | 89.9% |

These data indicate that the use of a combination of a mixture of 0.16 M glycine and as low as 0.04 M lysine with 1.2 g/ml (70% w/v, 55.6 w/w) of sucrose affords advantageous stability to heat of AHF that was heretofore not known.

EXAMPLE 6

Effect of Varying Amino Acid Concentration with High Sugar Concentration on Recovery of Antihemophilic Factor This experiment was carried out to determine the effects varying low concentrations of glycine or arginine or a combination thereof in the presence of an AHF solution having an $A_{280}$ at 10.1 and containing 0.01 M of citrate and 1.2 g/ml of sucrose at pH adjusted to 7.18. The solutions were heated at pasteurization conditions for 10 hours at 60° C. The results are given below:

|  | % AHF Recovery |
|---|---|
| citrate only | 41.1% |
| 0.1 M glycine | 45.0% |
| 0.3 M glycine | 61.3% |
| 0.5 M glycine | 75.4% |
| 0.05 M arginine | 64.2% |
| 0.1 M arginine | 71.0% |
| 0.15 M glycine + 0.05 M arginine | 61.5% |

These data indicate that the use of as low a concentration as 0.3 M of glycine alone, or as low a concentration as 0.05 M arginine alone, or a concentration of 0.15 M glycine together with 0.05 M arginine, each in combination with 1.2 g/ml (70% w/v, 55.6% w/w) of sucrose, affords advantageous stability to heat of AHF that was heretofore not known.

EXAMPLE 7

Effect of High Sugar Concentration and Amino Acid on Recovery of Fibronectin Activity This experiment was carried out to illustrate the effects of various combinations of heat stabilizing amino acids and sugars or sugar alcohols on fibronectin. Fibronectin was prepared by the method of Engvall et al, *Int. J. Cancer*, 20, 2 (1977) using the gelatin-Sepharose ® affinity medium method. Fibronectin was eluted from the affinity medium using 4 M urea and urea was removed by diafiltration. The resulting fibronectin was assayed and found to be greater than 95% pure. Samples were formulated and treated under pasteurization conditions for 10 hours at 60° C. as set forth in the table below:

|  |  | Recovery of therapeutic activity | |
|---|---|---|---|
| Run | Pasteurization Conditions (60° C., 10 hours) | a Agglutination assay (%) | b Rat Liver slice assay (%) |
| A | 57% sucrose (0.81 g/ml) | 105 | 120 |
| B | 57% sucrose, 0.5 M arginine | 118 | 60 |
| C | 0.5 M arginine | 10 | — |
| D | 0.5 M lysine | 5 | — |
| E | control (no heat stabilizer) | <1 | 0 |
| F | control, held at 5° C. for 10 hours | 100 | 100 | a = Agglutination Assay described by Check et al in the J. Reticuloendothelial Soc., Vol. 25, pages 351-362 (1979).
b = Rat Liver Slice Assay described by Molnar et al in Biochemistry, Vol. 18, page 3909 (1979).

These date indicate that the use of a low concentration of amino acid and higher (57%) concentration of sucrose as stabilizer against heat under pasteurization conditions affords advantages which were not heretofore known.

What is claimed is:

1. A method of pasteurizing a composition comprising a thermally sensitive, therapeutically active protein selected from the group consisiting of antihemophilic factor (Factor VIII), fibronectin, antithrombin III, alpha-1-antitrypsin, and prekallikrein, which comprises
    (a) mixing the protein composition with from 0.1 to 0.5 M of at least one amino acid and a compound selected from the group consisting of sugars and reduced sugars in an aqueous medium, said compound being present in the mixture in an amount of about 54% to saturation, on a weight to volume basis, and
    (b) heating the mixture at a temperature of about 60°-75° C. and a pH of about 5.5-8.0 for at least about 10 hours to pasteurize the protein composition and render it substantially free of infective hepatitis.

2. The method of claim 1 wherein the molecular weight of the compound is about 5000 or less.

3. The method of claim 1 wherein the pH of the mixture is about 6.0-7.5.

4. The method of claim 1 wherein the compound is sucrose.

5. The method of claim 1 wherein the amino acid is selected from the group consisting of arginine, lysine and glycine.

6. The method of claim 1 wherein the amount of compound is sufficient to result in the retention of at least about 40% of the activity of the protein during pasteurization of the protein composition.

7. The method of claim 1 wherein the mixture is heated in Step (b) at a temperature of about 60° C.

8. The method of claim 1 which further includes at least one of the steps of removing said compound from the mixture resulting from Step (b), removing said amino acid from the mixture resulting from Step (b), and removing both said compound and said amino acid from the mixture resulting from Step (b).

9. The method of claim 8 wherein the compound and/or amino acid is removed from the mixture of Step (b) by subjecting the mixture to diafiltration.

10. The method of claim 8 wherein the compound and/or amino acid is removed from the mixture of Step (b) by subjecting the mixture to dialysis.

11. The method of claim 8 which further includes the step of removing water from the mixture of Step (b).

12. The method of claim 11 wherein water is removed from the mixture of Step (b) by subjecting the mixture to ultrafiltration.

13. The method of claim 11 wherein water is removed from the mixture of Step (b) by subjecting the mixture to freeze-drying.

14. The method of claim 1 wherein the amount protein composition present in the mixture in Step (a) is from about 1 mg/ml to about 15 mg/ml based on total mixture, the amount of said amino acid present in the mixture in Step (a) is from about 0.1 to 0.5 M based on total mixture, and the amount of said compound present in the mixture in Step (a) is from about 0.8 g/ml to about 1.5 g/ml based on total mixture.

15. The method of claim 1 wherein said protein is selected from antihemophilic factor and fibronectin and is present in the mixture in Step (a) in the range of from about 1 mg/ml to about 15 mg/ml based on total mixture, and wherein said amino acid is selected from arginine, lysine and glycine and is present in the mixture in Step (a) in the range of from about 0.05 M to about 0.8 M based on total mixture.

16. The method of claim 15 wherein the mixture is heated in Step (b) at a temperature of about 60° C.

17. The method of claim 16 which further includes at least one of the steps of removing said compound from the mixture resulting from Step (b), removing said amino acid from the mixture resulting from Step (b), and removing both said compound and said amino acid from the mixture resulting from Step (b).

18. The method of claim 16 which further includes the step of removing water from the mixture of Step (b).

19. The method of claim 17 which further includes the step of removing water from the mixture of Step (b).

* * * * *